United States Patent
Nam et al.

(10) Patent No.: US 11,370,730 B2
(45) Date of Patent: Jun. 28, 2022

(54) METHOD FOR PREPARING 1,3-BUTADIENE

(71) Applicant: LG CHEM, LTD., Seoul (KR)

(72) Inventors: Hyunseok Nam, Daejeon (KR); Jun Han Kang, Daejeon (KR); Kyong Yong Cha, Daejeon (KR); Jaewon Jeong, Daejeon (KR); Dong Hyun Ko, Daejeon (KR); Jun Kyu Han, Daejeon (KR); Sang Jin Han, Daejeon (KR); Kyung Moo Lee, Daejeon (KR); Joohyuck Lee, Daejeon (KR); Daeheung Choi, Daejeon (KR); Myungji Suh, Daejeon (KR); Ye Seul Hwang, Daejeon (KR); Sunhwan Hwang, Daejeon (KR); Seongmin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/771,141

(22) PCT Filed: Feb. 1, 2019

(86) PCT No.: PCT/KR2019/001437
§ 371 (c)(1),
(2) Date: Jun. 9, 2020

(87) PCT Pub. No.: WO2019/168276
PCT Pub. Date: Sep. 6, 2019

(65) Prior Publication Data
US 2021/0163378 A1    Jun. 3, 2021

(30) Foreign Application Priority Data

Feb. 27, 2018 (KR) .................. 10-2018-0023838

(51) Int. Cl.
C07C 5/48 (2006.01)
C07C 7/04 (2006.01)
B01D 5/00 (2006.01)

(52) U.S. Cl.
CPC ............... $C07C\ 5/48$ (2013.01); $B01D\ 5/006$ (2013.01); $B01D\ 5/0075$ (2013.01); $C07C\ 7/04$ (2013.01)

(58) Field of Classification Search
CPC ............... C07C 5/48; C07C 7/04; B01D 5/00
See application file for complete search history.

(56) References Cited

U.S. PATENT DOCUMENTS 3,557,238 A * 1/1971 Cunningham ............ C07C 5/48
585/621
2014/0100399 A1   4/2014 Brummer et al.
(Continued)

FOREIGN PATENT DOCUMENTS

JP    60-115531 A    6/1985
JP    2011-001341 A    1/2011
(Continued)

Primary Examiner — Youngsul Jeong
(74) Attorney, Agent, or Firm — Dentons US LLP

(57) ABSTRACT

The present specification provides a method for preparing 1,3-butadiene, the method comprising: (A) obtaining a first product comprising a light component, 1,3-butadiene, and a heavy component from a reactant comprising butene; (B) separating the heavy component from a second product comprising the 1,3-butadiene and the light component by condensing the heavy component after heat exchanging the first product; and (C) separating concentrated heavy component by reboiling the condensed heavy component.

13 Claims, 1 Drawing Sheet

(56) References Cited

U.S. PATENT DOCUMENTS

| | | | |
|---|---|---|---|
| 2014/0100405 A1 | 4/2014 | Brummer et al. | |
| 2014/0200381 A1* | 7/2014 | Josch | C07C 7/11 |
| | | | 585/621 |
| 2016/0122565 A1 | 5/2016 | Abdelghani | |
| 2016/0152529 A1 | 6/2016 | Senetar | |
| 2016/0152531 A1 | 6/2016 | Walsdorff et al. | |
| 2016/0347686 A1 | 12/2016 | Grune et al. | |
| 2017/0036972 A1 | 2/2017 | Han et al. | |
| 2018/0002254 A1 | 1/2018 | Josch et al. | |
| 2018/0282246 A1 | 10/2018 | Ungelenk et al. | |
| 2019/0039971 A1 | 2/2019 | Josch et al. | |

FOREIGN PATENT DOCUMENTS

| | | |
|---|---|---|
| KR | 20130036470 A | 4/2013 |
| KR | 20150080495 A | 7/2015 |
| KR | 10-1577759 B1 | 12/2015 |
| KR | 20160083224 A | 7/2016 |
| KR | 20160106728 A | 9/2016 |
| KR | 20160114272 A | 10/2016 |
| KR | 20170063608 A | 6/2017 |
| KR | 20170084076 A | 7/2017 |
| KR | 10-1789892 B1 | 11/2017 |
| WO | 2016-071268 A1 | 5/2016 |
| WO | 2017133997 A1 | 8/2017 |

* cited by examiner

[Figure 1]
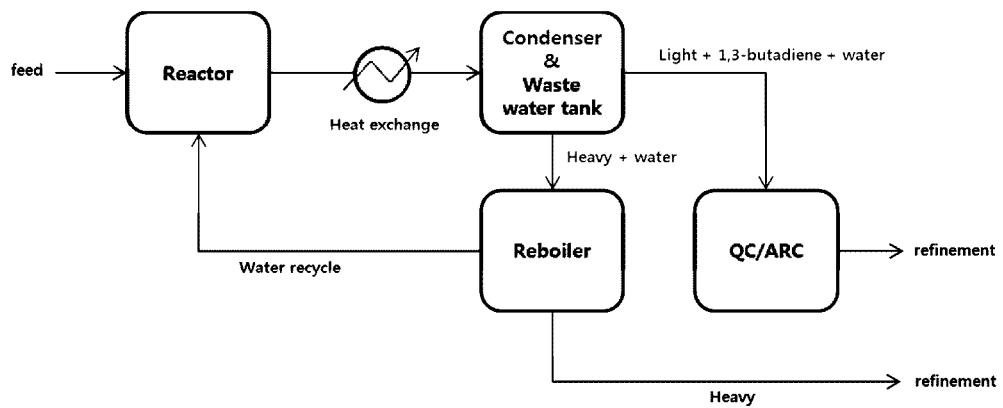
[Figure 2]
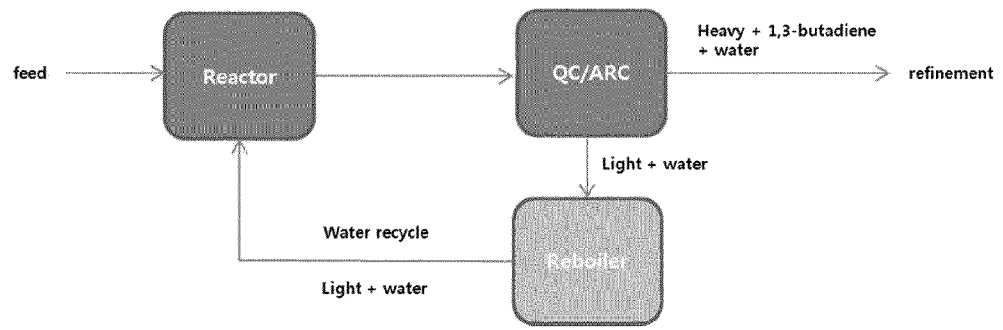

METHOD FOR PREPARING 1,3-BUTADIENE

The present application is a National Phase entry pursuant to 35 U.S.C. § 371 of International Application No. PCT/KR2019/001437 filed Feb. 1, 2019, and claims priority to and the benefit of Korean Patent Application No. 10-2018-0023838 filed in the Korean Intellectual Property Office on Feb. 27, 2018, the entire contents of which are incorporated herein by reference.

FIELD

The present specification relates to a method for preparing 1,3-butadiene.

BACKGROUND 1,3-butadiene is an intermediate of petroleum chemical products, and demand for 1,3-butadiene, and the value thereof, are gradually increasing globally. 1,3-butadiene has been prepared by using naphtha cracking, the direct dehydrogenation reaction of butene, the oxidative dehydrogenation reaction of butene, and the like.

However, since the naphtha cracking process consumes a lot of energy due to high reaction temperature, and is not a single process for producing only 1,3-butadiene, there is a problem in that other fundamental oil components in addition to 1,3-butadiene are produced in excess. Further, the direct dehydrogenation reaction of n-butene is thermodynamically disadvantageous and requires high temperature and low pressure conditions for producing 1,3-butadiene at high yield as an endothermic reaction, and thus is not suitable as a commercial process for producing 1,3-butadiene.

Accordingly, a technology for preparing 1,3-butadiene by using the oxidative dehydrogenation reaction of butene has been widely known. Meanwhile, the oxidative dehydrogenation reaction process of butene comprises a process of recycling waste water generated at the later stage of the quenching process and recovering the waste water as a reactant. However, the waste water (recycle water) recovered into the reactor comprises a light component, and a phenomenon in which the conversion rate of butene is decreased occurs.

Therefore, there is a need for a technology for removing a light component contained in the waste water.

SUMMARY

The present specification provides a method for preparing 1,3-butadiene.

An exemplary embodiment of the present specification provides a method for preparing 1,3-butadiene, the method comprising:

(A) obtaining a first product comprising a light component, 1,3-butadiene, and a heavy component from a reactant comprising butene;

(B) separating the heavy component from a second product comprising the 1,3-butadiene and the light component by condensing the heavy component after heat exchanging the first product; and (C) separating concentrated heavy component by reboiling the condensed heavy component.

A method for preparing 1,3-butadiene according to an exemplary embodiment of the present specification may obtain waste water except for a light component by using heat exchange and condensation of a product obtained from the oxidative dehydrogenation reaction of butene.

Accordingly, there is an effect of preventing the conversion rate of butene generated during the use of waste water (recycle water) from being decreased by stopping a light component contained in a reactant from reacting with oxygen (O2).

BRIEF DESCRIPTION OF THE DRAWINGS

FIG. 1 is a process diagram for performing a method for preparing 1,3-butadiene according to an exemplary embodiment of the present specification.

FIG. 2 is a process diagram for performing a method for preparing 1,3-butadiene according to Comparative Example 1 of the present specification.

DETAILED DESCRIPTION

Hereinafter, the present specification will be described in more detail.

In the present specification, the 'yield (%)' is defined as a value obtained by dividing the weight of 1,3-butadiene (BD) as a product of an oxidative dehydrogenation reaction by the weight of butene (BE) as a raw material. For example, the yield may be represented by the following equation.

Yield (%)=[(the number of moles of 1,3-butadiene produced)/(the number of moles of butene supplied)]×100

In the present specification, the 'conversion rate (%)' refers to a rate at which a reactant is converted into a product, and for example, the conversion rate of butene may be defined by the following equation.

Conversion rate (%)=[(the number of moles of butene reacted)/(the number of moles of butene supplied)]×100

In the present specification, the 'selectivity (%)' is defined as a value obtained by dividing the change amount of butadiene by the change amount of butene. For example, the selectivity may be represented by the following equation.

Selectivity (%)=[(the number of moles of 1,3-butadiene or COx produced)/(the number of moles of butene reacted)]×100

An exemplary embodiment of the present specification provides a method for preparing 1,3-butadiene, the method comprising: (A) obtaining a first product comprising a light component, 1,3-butadiene, and a heavy component from a reactant comprising butene; (B) separating the heavy component from a second product comprising the 1,3-butadiene and the light component by condensing the heavy component after heat exchanging the first product; and (C) separating concentrated heavy component by reboiling the condensed heavy component.

An oxidative dehydrogenation reaction process of butene comprises a process of refining the product. In particular, the waste water (recycle water) generated at the later stage of the quenching process during the refinement process is reboiled by using a column in order to recycle the waste water, and then is fed to the reactor (feed). However, during this process, there occurs a phenomenon in which the light component contained in the waste water is fed to the reactant, and reacts with oxygen ($O_2$) in the reactor to decrease the conversion rate of butene as the reactant.

However, the present invention may recycle the waste water, without the light component, into the reactor by cooling the product obtained after the oxidative dehydrogenation reaction of butene through heat exchange and condensation before the quenching of the product. Accordingly, there is an advantage in that the conversion rate of butene generated during the use of waste water comprising the light component is prevented from being decreased by stopping the light component from reacting with oxygen in the reactant. In addition, since a column for removing the light component in the refinement process does not need to be installed, there is also an advantage in that the costs may be reduced.

According to an exemplary embodiment of the present specification, the condensation temperature of the heavy component in step (B) may be 60° C. to 100° C. Preferably, the condensation temperature may be 80° C. to 100° C., more preferably 90° C. to 100° C. When the condensation temperature satisfies the above range, the heavy component in the product obtained after the oxidative dehydrogenation reaction of butene is condensed, and may be effectively separated from the light component and 1,3-butadiene.

According to an exemplary embodiment of the present specification, the heat exchanging of the first product in step (B) may use a heat exchanger used in the art. Examples of the heat exchanger comprise a shell & tube type heat exchanger, a block type heat exchanger, a jacket type heat exchanger, an air cooled type heat exchanger, a spiral type heat exchanger, a plate type heat exchanger, and the like, but are not limited thereto. Furthermore, one or two or more heat exchangers may be used.

According to an exemplary embodiment of the present specification, the temperature of the first product may be 200° C. to 400° C. Specifically, the temperature of the first product may be 230° C. to 370° C.

According to an exemplary embodiment of the present specification, the heat exchanging of the first product in step (B) may mean cooling the first product. The temperature of the first product obtained in step (A) may be 200° C. to 400° C., and the first product may be cooled through heat exchange, such that the temperature after the heat exchange step in step (B) is 60° C. to 100° C. Only when the temperature of the first product is cooled to the above range after the heat exchanging step, a condensation process which is the subsequent process can be performed, and in particular, the temperature of the first product may be an optimal temperature for condensing the heavy component.

According to an exemplary embodiment of the present specification, in the condensing of the heavy component, a condenser used in the art may be employed. Examples of the condenser comprise a water cooling type condenser, an air cooling type condenser, an evaporation type condenser, and the like, but are not limited thereto. The inside of the condenser may satisfy a temperature of 60° C. to 100° C., preferably a temperature of 80° C. to 100° C., and more preferably a temperature of 90° C. to 100° C. and a pressure of 0.1 kgf/cm$^2$ to 1.0 kgf/cm$^2$, but the temperature and the pressure are not limited thereto.

According to an exemplary embodiment of the present specification, the heavy component condensed in step (B) comprises condensed water, and it is possible to further comprise recovering water vapor obtained by reboiling the condensed heavy component in step (C), and feeding the water vapor to the reactant comprising butene. Specifically, when the condensed heavy component is reboiled, the concentrated heavy component and the water vapor may be separated.

According to an exemplary embodiment of the present specification, when the water vapor separated from the concentrated heavy component is fed again to the reactant comprising butene, it is possible to stop the light component from reacting with oxygen in the reactant. It is possible to prevent the conversion rate of butene generated during the use of waste water comprising the light component from being decreased by stopping the light component from reacting with oxygen in the reactant.

According to an exemplary embodiment of the present specification, the method for preparing 1,3-butadiene may further comprise obtaining 1,3-butadiene by refining the second product. The refining of the second product may comprise quenching the product. The refining of the second product is not limited in method as long as the refining of the second product is a typical method used in refining 1,3-butadiene from impurities in the art.

According to an exemplary embodiment of the present specification, step (A) may further comprise pre-heating the reactant comprising butene. When the pre-heating of the reactant is performed, an oxidative dehydrogenation reactant comprising butene is activated, and as a result, an efficient reaction may occur in a short period of time.

According to an exemplary embodiment of the present specification, a pressure of the pre-heating of the reactant may be 0.5 kgf/cm$^2$ to 1.5 kgf/cm$^2$. When the pressure of the pre-heating of the reactant satisfies the above range, an oxidative dehydrogenation reactant comprising butene is activated, and as a result, an efficient reaction may occur in a short period of time.

According to an exemplary embodiment of the present specification, obtaining the first product in step (A) may be performed in one reactor.

According to an exemplary embodiment of the present specification, obtaining the first product in step (A) may be performed in two or more reactors, that is, a multi-stage reactor. The multi-stage reactors may also be connected in series or in parallel, and the connection method is not limited thereto as long as the multi-stage reactor is a reactor used in the art.

According to an exemplary embodiment of the present specification, a pressure of obtaining the first product in step (A) may be 0.2 kgf/cm$^2$ to 1.5 kgf/cm$^2$. Preferably, the pressure may be 0.4 kgf/cm$^2$ to 1.0 kgf/cm$^2$. When the pressure satisfies the above pressure range, the optimized conversion rate and selectivity may be maintained. Further, when the pressure is less than 0.2 kgf/cm$^2$, the conversion rate of butene may be decreased, and when the pressure is more than 1.5 kgf/cm$^2$, the butadiene selectivity may be decreased.

According to an exemplary embodiment of the present specification, the reactant comprising butene may be a raw material comprising $C_4$ fractions, steam, oxygen ($O_2$), and nitrogen ($N_2$).

According to an exemplary embodiment of the present specification, the light component may be one or more components selected from the group consisting of hydrogen, oxygen, nitrogen, carbon dioxide, carbon monoxide, water vapor, methane, ethylene, acetaldehyde, 1-butene, 2-butene, and vinylacetylene. However, the light component is not limited thereto, and may further comprise impurities of a light component typically added in the oxidative dehydrogenation reaction of butene.

According to an exemplary embodiment of the present specification, the heavy component may be one or more components selected from the group consisting of acrolein, furan, butanone, benzene, 4-vinylcyclohexene, styrene, 4-formylcyclohexene, benzofuran, 3-acetyl-1-cyclohexene, cyclohexene dicarboxy, benzophenone, and 9-fluorenone. However, the heavy component is not limited thereto, and may further comprise impurities of a heavy component typically added in the oxidative dehydrogenation reaction of butene.

According to an exemplary embodiment of the present specification, the light component may mean a compound having a molecular weight lower than that of 1,3-butadiene, and the heavy component may mean a compound having a molecular weight higher than that of 1,3-butadiene.

According to an exemplary embodiment of the present specification, a bismuth-molybdenum catalyst, a ferrite-based catalyst, and the like, generally known during the oxidative dehydrogenation reaction of butene may be used as the catalyst, but are not limited thereto.

According to an exemplary embodiment of the present specification, preparing the butadiene may allow a raw material comprising $C_4$ fractions, steam, oxygen ($O_2$), and nitrogen ($N_2$) to react under the conditions of a reaction temperature of 300° C. to 500° C., a pressure of 0.1 kgf/cm² to 1.5 kgf/cm², and a gas hourly space velocity (GHSV) of 30 $h^{-1}$ to 200 $h^{-1}$.

The $C_4$ fractions may mean $C_4$ raffinate-1,2,3 remaining by separating useful compounds from a $C_4$ mixture produced by naphtha cracking, and may mean $C_4$ classes which may be obtained through ethylene dimerization.

According to an exemplary embodiment of the present specification, the $C_4$ fractions may be one or a mixture of two or more selected from the group consisting of n-butane, trans-2-butene, cis-2-butene, and 1-butene.

According to an exemplary embodiment of the present specification, the steam or nitrogen ($N_2$) is a diluted gas introduced for the purpose of reducing the explosion danger of the reactant, simultaneously preventing coking of the catalyst, removing the reaction heat, and the like, in the oxidative dehydrogenation reaction.

According to an exemplary embodiment of the present specification, the oxygen ($O_2$) is an oxidant and reacts with $C_4$ fractions to cause a dehydrogenation reaction.

According to an exemplary embodiment of the present specification, the oxidative dehydrogenation reaction may proceed according to the following Reaction Formula 1 or Reaction Formula 2.

$$C_4H_8 + \tfrac{1}{2}O_2 \rightarrow C_4H_6 + H_2O \qquad \text{[Reaction Formula 1]}$$

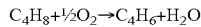

$$C_4H_{10} + O_2 \rightarrow C_4H_6 + 2H_2O \qquad \text{[Reaction Formula 2]}$$

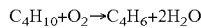

Hydrogen of butane or butene is removed from the oxidative dehydrogenation reaction, and as a result, butadiene is prepared. Meanwhile, the oxidative dehydrogenation reaction may produce a side reaction product comprising carbon monoxide (CO), carbon dioxide ($CO_2$), or the like, except for the main reaction such as Reaction Formula 1 or 2. The oxidative dehydrogenation reaction may comprise a process in which the side reaction product is separated so as not to be continuously accumulated in the process, and is released out from the system.

According to an exemplary embodiment of the present specification, in the method for preparing butadiene, the conversion rate of butene may be 83% or more, preferably 83.2% or more.

According to an exemplary embodiment of the present specification, in the method for preparing butadiene, the butadiene selectivity may be 89% or more, preferably 89.4% or more.

According to an exemplary embodiment of the present specification, the yield of butadiene may be 74% or more, preferably 74.4% or more.

FIG. 1 is an exemplary process diagram for performing a method for preparing 1,3-butadiene according to an exemplary embodiment of the present specification.

According to FIG. 1, a raw material comprising $C_4$ fractions, steam, oxygen ($O_2$), and nitrogen ($N_2$) is fed to a reactor, and an oxidative dehydrogenation reaction occurs therein. The reactor may be one reactor, and may be two or more multi-stage reactors. The method may further comprise pre-heating the raw material as a reactant before the reactor.

A first product obtained after an oxidative dehydrogenation reaction is cooled via a heat exchanger before the quenching (QC) step. Subsequently, when the first product passes through a condenser, a heavy component is separated from a light component and 1,3-butadiene. In this case, the temperature of the condenser may be 60° C. to 100° C., 80° C. to 100° C., and 90° C. to 100° C. The temperature range is a temperature range within which the heavy component may be condensed and separated.

Next, the heavy component is concentrated from the separated heavy component through a reboiler, and water vapor is separated. The separated water vapor (water recycle) may be fed again to the reactant, and may be recycled.

According to FIG. 1, the light component and 1,3-butadiene separated from the condenser is subjected to a general refinement process, and 1,3-butadiene may be separated.

As described above, according to an exemplary embodiment of the present specification, the method for preparing 1,3-butadiene is performed for the purpose of obtaining waste water in which a light component is not contained therein through heat exchange and condensation prior to the refinement step, particularly, the quenching step, in a process after the oxidative dehydrogenation reaction of butene. The waste water in which the light component is not included is recovered again into the reactant of the reactor, and thus recycled in the oxidative dehydrogenation reaction, and in this case, it is possible to prevent a phenomenon in which the light component reacts with oxygen (02) in the reactor to decrease the conversion rate of butene as a reactant because the light component is not comprised.

EXAMPLES

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

EXAMPLES

Experimental Example 1

An oxidative dehydrogenation reaction was performed under the conditions of 350° C., GHSV=120 $h^{-1}$, OBR=1, SBR=5, and NBR=4.

Water vapor obtained by heating distilled water which did not comprise a light component and a heavy component was fed to a reactant.

Example 1

An oxidative dehydrogenation reaction was performed under the conditions of 350° C., GHSV=120 $h^{-1}$, OBR=1, SBR=5, and NBR=4.

As in the process in FIG. 1, a light component, gases, and a heavy component were separated from the obtained product through heat exchange and condensation in a sequence before the refinement process. More specifically, the temperature of the primary product before the heat exchange process was 360° C., and heat exchange was performed by using two shell & tube heat exchangers, or a device capable of having a better heat exchange effect. The temperature of the product that passed through the first heat exchanger was 250° C., and the temperature of the product that passed through the second heat exchanger was 90° C.

Water vapor obtained by heating the obtained heavy component was recovered into the reactor and fed to the reactant, and the concentrated heavy component was separated into a subsequent refinement process.

1,3-butadiene was prepared by subjecting the light component and 1,3-butadiene separated by the condensation process to a subsequent process (quenching).

Example 2

1,3-butadiene was prepared in the same manner as in Example 1, except that the temperature of the product that passed through the second heat exchanger was adjusted to 100° C. in Example 1.

Comparative Example 1

An oxidative dehydrogenation reaction was performed under the conditions of 350° C., GHSV=120 h$^{-1}$, OBR=1, SBR=5, and NBR=4.

As in the process in FIG. 2, without the heat exchange and condensation process, waste water comprising the light component separated by quenching the obtained product was recovered into the reactor, and fed to the reactant.

The obtained product was subjected to a refinement process to prepare 1,3-butadiene.

(GHSV=gas hourly space velocity, OBR=oxygen/total mixed-butene ratio, SBR=steam/total mixed-butene ratio, NBR=nitrogen/total mixed-butene ratio)

In Experimental Example 1 and Comparative Example 1, the results of measuring the conversion rate of butene, the butadiene selectivity, the yield of butadiene, the $CO_x$ selectivity, and the byproduct selectivity are shown in the following Table 1.

TABLE 1

| Classification | Butene conversion rate (%) | Butadiene selectivity (%) | Butadiene yield (%) | By product selectivity (%) | COx selectivity (%) |
|---|---|---|---|---|---|
| Experimental Example 1 | 83.2 | 89.4 | 74.4 | 0.58 | 10.0 |
| Comparative Example 1 | 82.2 | 89.2 | 73.3 | 0.71 | 10.1 |

Further, the simulated results of separating light and heavy components in Examples 1 and 2 and Comparative Example 1 are shown in the following Table 2. More specifically, the results in the following Table 2 were obtained by inputting the butene conversion rate, 1,3-butadiene selectivity, reaction temperature, composition of produced gas, and the like obtained through the experiment into ASPEN plus (process simulation program). That is, the flow rate of water produced from the reaction and the composition ratio of the light organic material are the results obtained through the experiment, and the composition ratio of the condensed water to the condensed light organic material is a result obtained by simulation. The smaller the content of the following light organic material is, that is, the closer to 0 the content is, the more preferred the results are.

TABLE 2

| Classification | Heat exchange temperature (° C.) | Condensed water (g/hr) | Light organic material (g/hr) | Content of light organic material (ppm) |
|---|---|---|---|---|
| Example 1 | 90 | 49.8 | 0.00226 | 49 |
| Example 2 | 100 | 13.0 | 0.00027 | 22 |
| Comparative Example 1 | — | 70.1 | 0.00485 | 69 |

According to Tables 1 and 2, as in Examples 1 and 2, when the waste water which does not comprise the light component is recycled again through heat exchange and condensation prior to the refinement step, particularly, the quenching step during the oxidative dehydrogenation reaction process of butene, the conversion rate of butene may be increased.

When Experimental Example 1 is compared with Comparative Example 1, it can be confirmed that in the case of Experimental Example 1 in which water vapor which does not comprise the light component is utilized, the conversion rate of butene is higher than that of Comparative Example 1 in which the waste water comprising the light component is recycled. Accordingly, it can be confirmed that the yield of butadiene is also high. Therefore, even in Examples 1 and 2 in which the content of the light organic material is lower than that of Comparative Example 1, an effect of a higher conversion rate of butene than that of Comparative Example 1 may be obtained.

This is because the light component reacts with oxygen ($O_2$) in the reactor to decrease the conversion rate of butene as a reactant, and it is possible to prevent a phenomenon in which the conversion rate of butene is decreased when the light component is not comprised or a partially separated water vapor is recycled in the reactant as in Experimental Example 1 and Examples 1 and 2.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for preparing 1,3-butadiene, the method comprising:
   (A) feeding reactants into a reactor and performing an oxidative dehydrogenation reaction within the rector to produce a first product comprising water, a light component, 1,3-butadiene, and a heavy component, wherein the light component is one or more components selected from the group consisting of hydrogen, oxygen, carbon dioxide, carbon monoxide, methane, ethylene, acetaldehyde, 1-butene, 2-butene, and vinylacetylene, and the heavy component is a component having a molecular weight higher than that of the 1,3-butadiene;
   (B) cooling the first product by feeding the first product through a heat exchanger to produce a cooled first product having a temperature of 60° C. to 100° C., wherein the heat exchanger comprises a shell and tube heat exchanger, a block heat exchanger, a jacket heat exchanger, an air cooled heat exchanger, a spiral heat exchanger, or a plate heat exchanger;

(C) feeding the cooled first product from the heat exchanger to a condenser operating at a temperature of 60° C. to 100° C. and a pressure of 0.1 kgf/cm$^2$ to 1.0 kgf/cm$^2$, and separating the heavy component from the 1,3-butadiene and the light component by condensing the heavy component, thus producing a first stream from the condenser comprising the heavy component and water and a second stream from the condenser comprising the light component, 1,3-butadiene and water;

(D) feeding the first stream from the condenser to a reboiler, and reboiling the first stream to separate the heavy component from the water; and (E) feeding the separated water from the first stream to the reactor.

2. The method of claim 1, further comprising obtaining 1,3-butadiene by refining the second stream.

3. The method of claim 1, wherein step (A) further comprises pre-heating the reactants, and the reactants comprise butene.

4. The method of claim 1, wherein the heavy component is one or more components selected from the group consisting of acrolein, furan, butanone, benzene, 4-vinylcyclohexene, styrene, 4-formylcyclohexene, benzofuran, 3-acetyl-1-cyclohexene, cyclohexene dicarboxy, benzophenone, and 9-fluorenone.

5. The method of claim 1, wherein the reactants comprise a ferrite-based catalyst.

6. The method of claim 3, wherein the preheating is performed at a pressure of 0.5 kgf/cm$^2$ to 1.5 kgf/cm$^2$.

7. The method of claim 1, wherein the first product is obtained in step (A) under a pressure of 0.2 kgf/cm$^2$ to 1.5 kgf/cm$^2$.

8. The method of claim 1, wherein the reactants comprise C$_4$ fractions, steam, oxygen, and nitrogen.

9. The method of claim 8, wherein the first product is obtained in step (A) under a pressure of 0.4 kgf/cm$^2$ to 1.0 kgf/cm$^2$.

10. The method of claim 1, wherein the reactants comprise butene, and wherein the method for preparing 1,3-butadiene has a conversion rate of the butene of 83% or more, wherein the conversion rate is calculated as follows:

$$\text{Conversion rate (\%)} = [(\text{number of moles of butene reacted})/(\text{number of moles of butene supplied})] \times 100.$$

11. The method of claim 1, wherein the reactants comprise butene, and wherein the method for preparing 1,3-butadiene has a 1,3-butadiene selectivity of 89% or more, wherein the selectivity is calculated as follows:

$$\text{Selectivity (\%)} = [(\text{number of moles of 1,3-butadiene or COx produced})/(\text{number of moles of butene reacted})] \times 100.$$

12. The method of claim 1, wherein the reactants comprise butene, and wherein the method for preparing 1,3-butadiene has a yield of 1,3-butadiene of 74% or more, wherein the yield is calculated as follows:

$$\text{Yield (\%)} = [(\text{the number of moles of 1,3-butadiene produced})/(\text{the number of moles of butene supplied})] \times 100.$$

13. The method of claim 1, wherein the reactants comprise butene, and wherein the method for preparing 1,3-butadiene has a conversion rate of the butene of 83% or more, a 1,3-butadiene selectivity of 89% or more, and a yield of 1,3-butadiene of 74% or more, wherein the conversion rate, selectivity and yield are calculated as follows:

$$\text{Conversion rate (\%)} = [(\text{number of moles of butene reacted})/(\text{number of moles of butene supplied})] \times 100;$$

$$\text{Selectivity (\%)} = [(\text{number of moles of 1,3-butadiene or COx produced})/(\text{number of moles of butene reacted})] \times 100; \text{ and}$$

$$\text{Yield (\%)} = [(\text{the number of moles of 1,3-butadiene produced})/(\text{the number of moles of butene supplied})] \times 100.$$

* * * * *